United States Patent [19]
Widder et al.

[11] Patent Number: 5,732,707
[45] Date of Patent: Mar. 31, 1998

[54] METHOD OF ULTRASONICALLY QUANTITATING MYOCARDIAL PERFUSION USING AS INTRAVENOUSLY INJECTED TRACER

[75] Inventors: Kenneth J. Widder, Rancho Santa Fe; Harold B. Levene; Gary L. Bales, both of San Diego, all of Calif.

[73] Assignee: Molecular Biosystems, Inc., San Diego, Calif.

[21] Appl. No.: 659,542

[22] Filed: Jun. 5, 1996

Related U.S. Application Data

[63] Continuation of Ser. No. 415,592, Apr. 3, 1995, abandoned, which is a continuation-in-part of Ser. No. 237,351, May 3, 1994, abandoned.

[51] Int. Cl.$^6$ .................................................. A61B 8/00
[52] U.S. Cl. ........................... 128/661.08; 128/662.02
[58] Field of Search ........................ 128/653.1, 653.4, 128/654, 662.02, 661.09, 661.1, 661.08

[56] References Cited

U.S. PATENT DOCUMENTS

| | | |
|---|---|---|
| 4,316,391 | 2/1982 | Tickner . |
| 4,957,656 | 9/1990 | Cerny et al. . |
| 5,040,537 | 8/1991 | Katakura . |
| 5,135,000 | 8/1992 | Akselrod et al. . |
| 5,137,928 | 8/1992 | Erbel et al. . |
| 5,149,543 | 9/1992 | Cohen et al. . |
| 5,190,982 | 3/1993 | Erbel et al. . |
| 5,315,997 | 5/1994 | Widder et al. . |
| 5,413,774 | 5/1995 | Schneider et al. ............ 128/662.02 |

FOREIGN PATENT DOCUMENTS

| | | |
|---|---|---|
| 0458745 | 11/1991 | European Pat. Off. . |
| 0554213 | 8/1993 | European Pat. Off. . |
| WO 80/02365 | 11/1980 | WIPO . |
| WO 89/06978 | 8/1989 | WIPO . |
| WO 91/09629 | 7/1991 | WIPO . |
| WO 91/12823 | 9/1991 | WIPO . |
| WO 90/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |

OTHER PUBLICATIONS

Rovai et al., "Airfilled Serum Human Albumin Microspheres in the Coronary Circulation: Divergence from a Reference Radioactive Tracer." *Supplement 1 Circulation* 86(4):I–574 (abstract No. 2286) (1992).

Rovai et al., "Intracoronary Air–Filled Albumin Microspheres for Myocardial Blood Flow Measurement." *J. American College of Cardiology* 22(7):2014–2021 (1993).

Rovai et al., "Failure of Sonicated Albumin Microspheres to Quantify Coronary Blood Flow in Dogs." *European Heart Journal* 13(Abstracts Suppl):16 (abstract No. 220) (1992).

Rovai et al., "Difference Between Myocardial Transit Time of Sonicated Albumin Microspheres and of Radionucleotide Labelled Albumin." *European Heart Journal* 13(Abstracts Suppl):16(abstract No. 221) (1992).

Kaul et al., "Relationship of Washout Parameters During Myocardial Contrast Echocardiography to Regional Myocardial Blood Flow in a Model of Graded coronary Stenosis." *Clinical Research* 36(3):288A (1988).

(List continued on next page.)

*Primary Examiner*—George Manuel
*Attorney, Agent, or Firm*—Morrison & Foerster

[57] ABSTRACT

Myocardial perfusion is assessed quantitatively by an ultrasonic echocardiographic procedure in which: the myocardium is ultrasonically imaged; an ultrasonic contrast agent consisting of a suspension of pressure-stable, water-insoluble gas-containing microspheres sized to pass through the pulmonary capillaries is injected intravenously; imaging is continued through the first transit of the microspheres through the myocardium; the videodensity versus time relationship is determined from the images; and blood flow through the myocardium is calculated from that relationship.

10 Claims, 5 Drawing Sheets

OTHER PUBLICATIONS

Keller et al., "Intraoperative Assessment of Regional Myocardial Perfusion Using Quantitative Myocardial Contrast Echocardiography: An Experimental Evaluation." *J. American College of Cardiology* 16(5):1267–1279 (1990).

Edwards et al., "Myocardial Contrast Two–Dimensional Echocardiography Can Be Used to Measure Myocardial Red Blood Cell Transit In–Vivo ." *Supplement III Circulation* 82(4):III–96 (abstract No. 0379) (1990).

Kaul, "Constrast Echocardiography and Myocardial Perfusion." *Clinical Cardiology* 14(Suppl V):V–15–V–18 (1991).

Skyba et al., "Myocardial Blood Flow can be Quantified During Myocardial Contrast Echocardiography Using Left Atrial Injection of Contrast." *J. of American Society of Echocardiography* 6(3) Part 2:S8 (abstract No. 28) (1993).

Ismail et al., "Albunex® Microbubbles Mimic Red Blood Cell Transit Through the Human Myocardium." *Circulation* 88(4) Part 2:I–683 (abstract No. 0864) (1993).

Jayaweera et al., "*In Vivo* Myocardial Kinetics of Air–Filled Albumin Microbubbles During Myocardial Contrast Echocardiography: Comparison With Radiolabeled Red Blood Cells." *Circulation Research* 74(6):1157–1165 (1994).

Skyba et al., "Quantification of Myocardial Perfusion With Myocardial Contrast Echocardiography During Left Atrial Injection of Contrast: Implications for Venous Injection." *Circulation* 90(3):1513–1521 (1994).

Medline Database Abstract of Mudra et al., "Myocardial contrast echocardiography with sonicated iopromide (Ultravist 370) before and after coronary angioplasty" *Z. Kardiol.* (1991) 80:367–372.

Medline Database Abstract of Vitarelli et al., "2–Dimensional quantitative contrast echocardiography in the assesment of atrial septal defects" *J. Cardiovas. Ultrason.* (1984) 3:345–350.

Medline Database Abstract of Feinstein et al., "Myocardial contrast echocardiography:Examination of intracoronary injections, microbubble diameters, and video–intensity decay" *Am. J. Physiol. Imaging* (1986) 1:12–18.

Ophir et al., "Contrast agents in diagnostic ultrasound" *Ultrasound in Med. & Biol.* (1989) 15(4):319–333.

Feinstein et al., "Safety and efficacy of a new transpulmonary ultrasound contrast agent: Initial multicenter clinical results" *J. Am. College Cardiol.* (1990) 16(2):316–324.

Mor–Avi et al., "Myocardial regional blood flow: Quantitative measurement by computer analysis of contrast enhanced echocardiographic images" Ultrasound in Med. & Biol. (1993) 19(8):619–633.

de Jong et al., "Quantification of transpulmonary echocontrast effects" Ultrasound in Med. & Biol. (1993) 19(4):279–288.

Wilson et al., "A feasibility study on quantitating myocardial perfusion with Albunex®, an ultrasonic contrast agent" Ultrasound in Med. & Biol. (1993) 19(3):181–191.

Sanders et al., "Contrast opacification of left ventricular myocardium following intravenous administration of sonicated albumin microspheres" Am. Heart J. (1991) 122(6):1660–1665.

Silverman et al., "Intravenous Albunex® injections increase intramyocardial backscatter" Circulation (1989) 80:II–369.

Berwing et al., "Echocardiographic imaging of the left ventricle by peripheral intravenous injection of echo contrast agent" Am. Heart J. (1988) 115:399–408.

Camarano et al., "Estimation of myocardial blood volume by contrast echocardiography can provide an assessment of myocardial blood flow" J. Am. College Cardiol. (Feb 1994) p. 450A (abstract No. 816–4.).

Cheirif et al., "Assessment of myocardial perfusion in humans by contrast echocardiography. I. Evaluation of regional coronary reserve by peak contrast intensity" J. Am College Cardiol. (1988) 11(4):735–743.

Dittrich et al., "Myocardial perfusion using new intravenous ultrasound contrast agents: Comparision between video and integrated backscatter images with a prototype program" J. Am. College Cardiol. (Feb. 1994) p. 393A (abstract 797–2.).

Feinstein, "Myocardial perfusion imaging: Contrast echocardiography today and tomorrow" J. Am. College Cardiol. (1986) 8(1):251–253.

Heymann et al., "Blood flow measurements with radionuclide–labeled particles" Prog. in Cardiovascular Dis. (1977) 20(1):55–78.

Jayaweera et al., "Method for the quantitation of myocardial perfusion during myocardial contrast two–dimensional echocardiography" J. Am. Soc. Echocardiography (1990) 3(2):91–98.

Kaul et al., "Assessment of regional myocardial blood flow with myocardial contrast two–dimensional echocardiography" J. Am. College Cardiol. (1989) 13(2):468–482.

Keller et al., "Myocardial contrast echocardiography without significant hemodynamic effects of reactive hyperemia: A major advantage in the imaging of regional myocardial perfusion" J. Am. College Cardiol. (1988) 12(4):1039–1047.Keller et al., The behavior of sonicated albumin microbubbles within the microcirculation: A basis for their use during myocardial contrasts echocardiography Circulation Res. (1989) 65:458–467.

Marcus et al., "Methods of measurement of myocardial blood flow in patients: A critical review" Circulation (1987) 76(2):245–253.

Monaghan et al., "Digital subtraction contrast echocardiography: A new method for the evaluation of regional myocardial perfusion" Brit. Heart J. (1988) 59:12–19.

Mor–Avi et al., "Myocardial transit time of the echocardiagraphy contrast media" Ultrasound in Med. & Biol. (1993) 19(8):635–648.

Reisner et al., "Myocardial perfusion imaging by contrast echocardiography with use of intracoronary sonicated albumin in humans" J. Am. College Cardiol. (1989) 14(3):660–665.

Shapiro et al., "Reproducibility of quantitative myocardial contrast echocardiography" J. Am. College Cardiol. (1990) 15(3):602–609.

Vandenberg et al., "Quantitation of myocardial perfusion by contrast echocardiography: Analysis of contrast gray level appearance variables and intracyclic variability" J. Am. College Cardiol. (1989) 13(1):200–206.

Wiencek et al., "Pitfalls in quantitative contrast echocardiography: The steps to quantitation of perfusion" J. Am. Soc. Echocardiography (1993) 6:.395–416.

Wood, "Definition and symbols for terms commonly used in relation to indicator–dilution curves" Circulation Research (1962) 10:379–380.

METHOD OF ULTRASONICALLY QUANTITATING MYOCARDIAL PERFUSION USING AS INTRAVENOUSLY INJECTED TRACER

CROSS-REFERENCE TO RELATED APPLICATION

This application is a continuation of Ser. No. 08/415,592, filed Apr. 3, 1995 now abandoned, which is a continuation-in-part of U.S. patent application Ser. No. 08/237,351, filed 3 May 1994 now abandoned.

TECHNICAL FIELD

This invention is in the field of ultrasonic imaging for diagnostic purposes. More particularly it relates to methods of performing myocardial contrast echocardiography (MCE) utilizing an intravenously injected tracer in order to obtain quantitative information relating to blood flow in the myocardium.

BACKGROUND

Diagnostic ultrasonic imaging is based on the principle that waves of sound energy can be focused upon an area of interest and reflected in such a way as to produce an image thereof. The ultrasonic transducer is placed on a body surface overlying the area to be imaged, and ultrasonic energy in the form of sound waves is directed toward that area. As ultrasonic energy travels through the body, the velocity of the energy and acoustic properties of the body tissue and substances encountered by the energy determine the degree of absorption, scattering, transmission and reflection of the ultrasonic energy. The transducer then detects the amount and characteristics of the reflected ultrasonic energy and translates the data into images.

As ultrasound waves move through one substance to another, there is some degree of reflection at the interface. The degree of reflection is related to the acoustic properties of the substances defining the interface. If these acoustic properties differ, such as with a liquid-solid or liquid-gas interface, the degree of reflection is enhanced. For this reason, gas-containing contrast agents are particularly efficient at reflecting ultrasound waves. The presence of such contrast agents results in more intense differences between the degree of reflectivity of the substances encountered which in turn leads to more well-defined ultrasonic images.

Ophir and Parker describe two types of gas-containing imaging agents as being (1) free gas bubbles and (2) encapsulated gas bubbles (*Ultrasound in Medicine and Biology* 15(4): 319–333 1989), the latter being developed in an attempt to overcome instability and toxicity problems encountered using the former. Encapsulated gas bubbles, hereinafter referred to as "microspheres", consist of a microbubble of gas surrounded by a shell composed of protein or other biocompatible material. One such imaging agent is Albunex® contrast agent (Molecular Biosystems, Inc., San Diego, Calif.) which consists of a suspension of air-filled albumin microspheres.

Contrast echocardiography is evolving as an important diagnostic procedure for the assessment of cardiac pathophysiology. This procedure utilizes contrast agents, most often in the form of air-filled microspheres, to enhance the backscatter intensity of the ultrasonic signal during imaging. Ultrasonic images thus formed can be used to assess valvular regurgitations, septal defects, cardiac output and other qualitative measurements of regional cardiac function.

One such technique for imaging the left ventricle utilizes Albunex® microspheres which are capable of transpulmonary passage after intravenous injection (Feinstein et al., Journal of American College of Cardiology (1990) 16(2) :316–324).

A number of prior investigators have suggested using microsphere suspensions as possible indicators for the assessment of regional blood supply to myocardial tissue. Mor-Avi, V. et al. (Ultrasound in Med. & Biol. (1993) 19(8):619–633) report studies in which myocardial blood flow was quantitated using Albunex® microspheres via intracoronary injection. The report speculates that noninvasive intravenously injected Albunex® microspheres might be useful for assessing myocardial blood flow. Myocardial perfusion studies using intravenously injected Albunex® microspheres have generally concluded that the level of resulting myocardial backscatter was too low to permit reproducible quantitation of myocardial blood flow. de Jong, N. et al., Ultrasound in Med. & Biol. (1993) 19:279–288; Wilson, B. et al., Ultrasound in Med. & Biol. (1993) 19:181–191; Sanders, W. E. et al., American Heart Journal (1991) 122(6):1660–1665; and Silverman, P. R. et al., Circulation (1989) 80(4):II-369.

Accordingly, there is currently no acceptable methodology for quantitatively assessing myocardial function using a noninvasively administered ultrasound contrast agent. The present invention provides such methodology.

DISCLOSURE OF THE INVENTION

The invention is a method of quantitatively measuring blood flow in a myocardium of a patient comprising:

(a) initiating ultrasonic imaging of the myocardium;

(b) while said imaging is continued, intravenously injecting an effective amount of biocompatible tracer microspheres containing a water insoluble gas into the patient, the microspheres having
  (i) a mean diameter that permits them to pass through the pulmonary capillaries of the patient; and
  (ii) pressure stability;

(c) continuing said imaging during the first transit of the microspheres through the myocardium;

(d) determining a videodensity versus time relationship from the images obtained in steps (a)–(c); and (e) calculating the blood flow in the myocardium from said relationship.

Two procedures may be used for carrying out step (e). Both involve generating a standard against which the relationship determined per step (d) is compared. In one, the standard is developed simultaneously from ultrasound images obtained of a homogeneous blood pool upstream of the myocardium. In the other, the standard is developed from independent calibration of the myocardial transit of the microspheres versus myocardial transit of labeled red blood cells.

MODES FOR CARRYING OUT THE INVENTION

Figure 1:
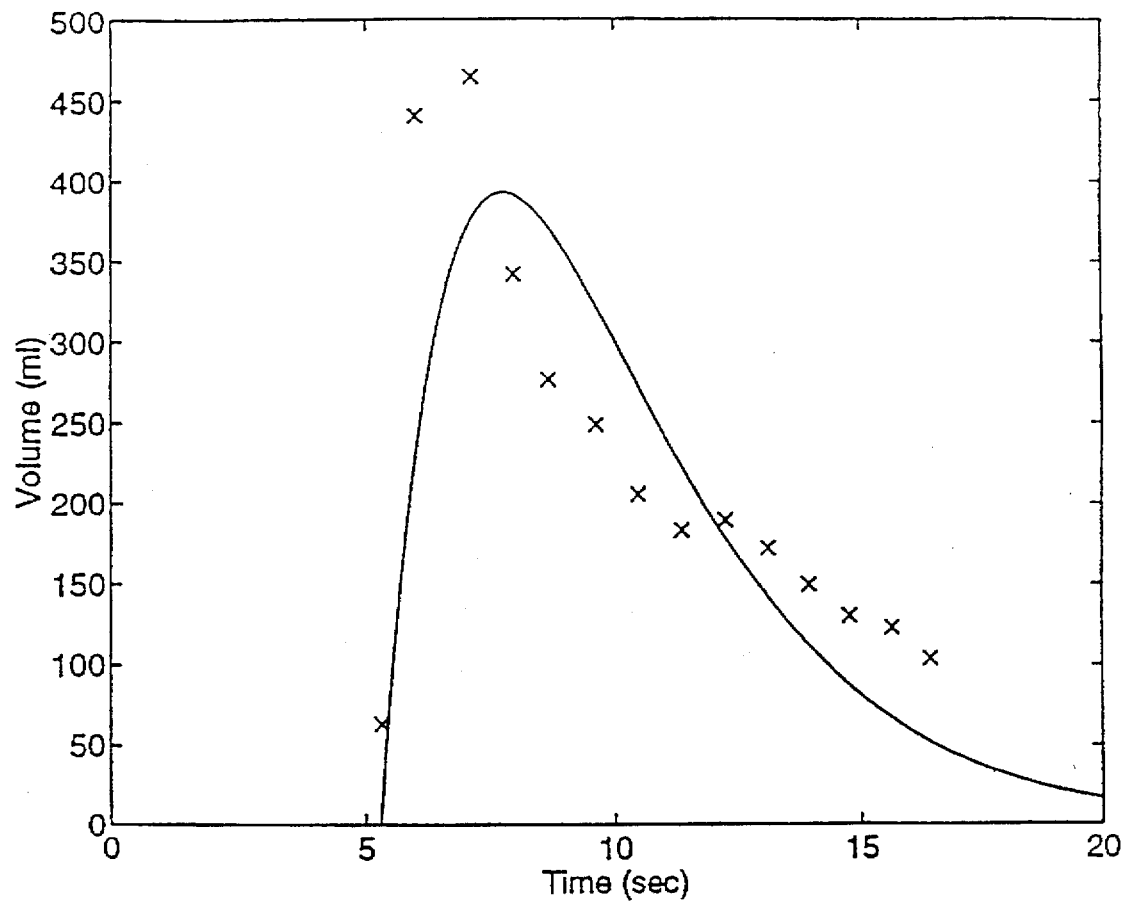
FIGS. 1–5 are graphs of data described in the Examples.

The present invention describes a method for quantitating myocardial perfusion from an intravenous injection of tracer microspheres. This quantitative method provides more information than the qualitative and semi-quantitative methods previously described which rely on relative differences in backscatter between different areas of tissues. The invention method provides a way of assessing physiological function in an objective sense, e.g., absolute blood flow.

Microspheres that are useful in the invention method have the following characteristics: (1) they are biocompatible, (2) they must be capable of passing through the pulmonary capillaries, and (3) they must be pressure stable. This combination of properties enable the microspheres to transit the myocardium at least once. The ultrasonic image of the myocardium before and during the first transit of the microspheres therethrough is of sufficient intensity and reproducibility to enable accurate quantitation of myocardial perfusion.

The microspheres are composed of microbubbles of a water insoluble gas surrounded by a discrete elastic shell. The insoluble gas must be pharmacologically acceptable, i.e., be biocompatible and minimally toxic to humans. The term "gas" refers to any compound which is a gas at atmospheric pressure at the temperature at which imaging is performed (typically normal physiological temperature). The gas may be composed of a single compound or a mixture of compounds. The gas is also insoluble in water, which intends a solubility of less than 0.01 ml of gas per ml of water at atmospheric pressure and a temperature of 25° C. Preferred gases are perhaloalkanes (e.g., perfluoroalkanes of 2 to 6 carbon atoms). Selected gases which are suitable for use in the present invention are given below in Table 1:

TABLE 1

| GAS | SOLUBILITY* ml of gas/ ml of water |
|---|---|
| Sulfur Hexafluoride | .0054 |
| Perfluoromethane | .00504 |
| Perfluoroethane | .00138 |
| Perfluoropropane | <.001 |
| Perfluorobutane | <.001 |

*Atmospheric pressure, 25° C.

The insoluble gas may constitute the entire gas component of the microspheres or only a fraction thereof. If it constitutes a fraction, it must be present in a sufficient proportion to render the microsphere pressure stable. That proportion will depend on the degree of water insolubility of the gas and the nature of the gas or gases with which it is mixed. Usually the water insoluble gas will constitute at least about 10 vol. % of the total gas content, more usually at least 30 vol. %, and preferably at least 50 vol. %.

The shells of the microspheres of the present invention may be composed of any of a variety of biocompatible polymers. Suitable polymers can include proteins, carbohydrates, lipids or mixtures thereof. Microbubbles of gas without a discrete shell would not be useful as tracers because of their pressure instability and their tendency to fluctuate in size which leads to an unpredictable acoustic response.

Suitable shell-forming polymers are well known in the art and are exemplified by those described in U.S. Pat. Nos. 4,957,656; 5,137,928; 5,190,982; 5,149,543; PCT Applications Nos. WO 92/17212; WO 92/18164; WO 91/09629; WO 89/06978; WO 92/17213; WO 91/12823; and WO 93/02712; and EPA Nos. 458,745 and 554,213. Human serum albumin is a preferred shell material.

The microspheres may be made by known methods used to make conventional air-filled microspheres such as sonication, mechanical cavitation or emulsion techniques. Such techniques are exemplified in the patent publications referred to above. In these procedures, air is replaced with the insoluble gas in an environment that is controlled against gas exchange with the atmosphere or dissolved gases in the system being used. Alternatively, it may be possible, with some materials, to first make air-filled microspheres and then exchange the air in the microspheres with the insoluble gas.

The maximum size (mean diameter) of the microsphere is defined by that size which will pass through the pulmonary capillaries. In the case of humans, that size will typically be less than about 10 micrometers. Correspondingly, the minimum size is that which will provide efficient acoustic scattering at the ultrasonic frequencies typically used for myocardial imaging. (The frequency may vary with the mode of imaging, e.g., transthoracic, transesophageal, and will normally be in the range of 2–12 MHz). The minimum size will typically be about 2 micrometers. Accordingly, the typical size range of the microspheres used in the invention method will be about 2 to about 10 micrometers, more usually 4 to 7 micrometers.

The tracer microspheres of the present invention must be capable of withstanding certain pressures in vivo. The high end of normal systolic pressure in a human is approximately 150 mm Hg, or 3.0 psi. In addition, transient intracardiac pressure pulses during systole could be expected to reach as high as 250 mm Hg or 5.0 psi. In order for microspheres to be suitable for use in the present invention, they must therefore be capable of withstanding a pressure of 5.0 psi. One way of determining pressure stability is to subject a microsphere suspension to a pressure of 5.0 psi for thirty (30) seconds and monitor the change in optical density of the suspension at 600 nm. A suspension which exhibits 25% of the initial $OD_{600}$ after the pressure is released would be considered stable. (See Example 2, infra.)

As indicated, the microspheres used in the invention are biocompatible. This intends that they be minimally toxic and have no other significant undesirable pharmacological or physiological effects, particularly with respect to causing any significant hemodynamic changes upon injection, such as hypertension, hypotension, tachycardia, brachycardia, arrythmia, myocardial shortening, ischemia or changes in pulmonary and microvasculature pressures.

Microspheres having the above-described characteristics are capable of being injected into the peripheral venous system, passing through the pulmonary capillaries, and having a sufficient lifetime to make a first transit through the myocardium. Because it is desirable to have the videodensity of the myocardium return to essentially baseline (i.e., its value before the microspheres are injected) during the echocardiographic procedure, it is preferable that the microspheres not have extended in vivo lifetimes that permit them to recirculate and prevent the videodensity from returning to baseline. The desirable lifetimes of the microspheres will depend upon the dosage volume of the injection, the site of injection and the recirculation time for the mammalian species being imaged. For humans, the desirable lifetime will typically be in the range of 10 to 90 sec. The recirculation times for several mammalian species are reported in Table 2 below.

TABLE 2

Recirculation Time by Species

| Species | Cardiac Output (l/min) | Stroke Volume (mL) | Heart Rate (beats/min) | Blood Volume (mL) | Recirculation (Sec) |
|---|---|---|---|---|---|
| Human  | 4.02[1] | 55.8[1] | 72[1]  | 5600[2] | 84  |
| Monkey | 1.00[1] | 8.8[1]  | 120[1] | 800[3]  | 48  |
| Dog    | 1.18[4] | 6.91[1] | 170[1] | 2000[5] | 101 |
| Cat    | 0.33[6] | 3.15[1] | 179[1] | 700[7]  | 127 |
| Rat    | 1.2[8]  | 0.21[8] | 346[8] | 20[9]   | 1   |

[1]Handbook of Biological Data. Spector, WI, W.B. Saunders Co., London, Philadelphia, 1956.
[2]Volume estimated for a 70 kg person.
[3]Volume estimated for a 10 kg cynamologous monkey.
[4]American Journal of Physiology. Sapirstein, 193:161–68 (1958).
[5]Volume estimated for a 25 kg dog.
[6]Circulatory Physiology: Cardiac Output and its Regulation. Guyton, A., Jones, C., Colman, T., W. B. Saunders Co., Toronto, London, Philadelphia, 1973.
[7]Volume estimated for an 8.8 kg cat.
[8]Hemodynamics. Milnor, W., Willram & Wilkins, Baltimore, MD, 1989.
[9]Volume estimated for 250 gm rat.

Effective dosage ranges of tracer microspheres can be determined experimentally in an animal model, and then calculated for humans or other animals based on the body weight relationship therebetween. The lower limit of the range is determined by the dosage that is sufficient to provide effective opacification of the myocardium. The upper limit is less than the dosage which gives unacceptable attenuation within the left ventricular cavity as evidenced by shadowing in the ultrasonic image. For perfluoropropane-containing albumin microspheres, the effective range for a 25 kg dog has been determined to be 0.3 to 1 ml, preferably 0.5 to 0.8 ml, of a suspension having a microsphere concentration of $5 \times 10^7$ to $5 \times 10^9$ per ml, preferably $5 \times 10^8$ to $1 \times 10^9$ per ml. On a unit body weight basis these ranges correspond to 12 to 40 µl per kg, preferably 20 to 32 µl per kg. It will be appreciated that the effective dosage range will vary depending upon the particular tracer microspheres employed and the patient being imaged. Extrapolating the above dog data to adult humans (assuming a body weight of 75 kg), indicates the adult human dosage range for such microsphere suspensions is 0.9 to 3 ml.

The method of the present invention can be described as consisting of two parts. The first part is acquiring the ultrasonic image. Two dimensional (2-D) or multidimensional (e.g., three-dimensional (3-D)) echocardiography equipment and procedures may be used to acquire the image. Such procedures and equipment are conventional. Currently three techniques are used to acquire 3-D images. In the first a standard transducer is used to collect tomographic images. The transducer is mounted on a track and collects images as it moves along the track. The speed of motion along the track is defined, so that the spacing between tomographic images is known. The collection of slices are then melded together to obtain a 3-D image, In the second, a standard transducer is also used to collect tomographic images. Attached to the transducer is a sensor that is able to report the spatial position of the transducer, so that the relative orientation of various images are known and the images can be melded together to generate a 3-D image. In the third, the transducer consists of a two dimensional array of elements. A one dimensional array of elements is able to acquire a tomographic image; the added dimension allows scanning in the third dimension. It is advantageous to use 3-D echocardiography in the "externally calibrated" method of quantifying myocardial blood flow (described below).

The myocardial image is acquired continuously from a time before injecting the tracer microspheres into venous circulation through the first transit of the microspheres through the myocardium and preferably until myocardial opacification has returned to baseline videodensity. The duration of the echocardiographic procedure may be estimated by determining the time the tracer microspheres need to travel from the site of injection to the heart and adding onto this time the average recirculation time for the test subject (given in Table 2 above). This acquired image is recorded, most usually on videotape, for later processing.

The second part of the invention method is processing the image. The image can be processed by any number of methods which are designed to convert videodensity data derived from the acquired image to a tracer volume versus time distribution from which an absolute measurement of blood flow can be calculated. All such methods require a "calibration" of the tracer microspheres, i.e., a determination of the relationship between videodensity (backscatter intensity) to tracer microsphere volume.

One way of carrying out the invention method can be referred to as the "internally calibrated" method. This refers to the procedure by which the relationship between videodensity and tracer microsphere volume is established from images obtained from a test subject and then used to calculate myocardial blood flow in the same test subject. Mor-Avi et al., supra, describe a method of "internally calibrating" tracer microspheres by using contrast agent-induced changes in videodensity over time (time-intensity curves) in a reference region (the left ventricular cavity or the aortic root) chosen to be representative of a homogeneous blood pool to calculate blood flow in the myocardial region of interest. This method may be subject to considerable error due to the lack of a linear relationship between backscatter and tracer microsphere concentration over the range necessary to calibrate the tracer microspheres. The non-linearity observed at higher microsphere concentrations is due to the effects of attenuation and signal intensity.

A second and novel image processing technique is referred to herein as the "externally calibrated" method. In this method, the tracer microspheres are calibrated, i.e. the relationship between videodensity and tracer microsphere volume is established, in a model system. Images subsequently acquired in a test subject using the calibrated tracer microspheres can then be processed to calculate absolute blood flow measurements. The externally calibrated method has the advantage that corrections can be made to account for non-linearities of the acoustic response at higher tracer microsphere concentrations and differences in rheology between tracer microspheres and red blood cells in the myocardium. In addition, once tracer microspheres are calibrated, they do not have to be re-calibrated in each new test subject.

The external calibration of tracer microspheres in an animal model is a two-step process. The first step is to determine the intracoronary transfer function ("ICTF") and the second step is to determine the intravenous transfer function ("IVTF"). A convolution of the ICTF with the IVTF defines the relationship between videodensity versus time collected after an intravenous administration and tracer microsphere volume versus time in the myocardium.

The ICTF defines the relationship between videodensity and tracer microsphere volume subsequent to a direct (intracoronary) injection of tracer microspheres. It accounts for any non-linearities and time dependence of the signal processing of the ultrasound instrument as well as any differences in the time dependence of myocardial transit between the tracer microspheres and red blood cells.

To establish the ICTF, a preferred method is to compare the flow of radiolabeled red blood cells (RBCs) to that of the flow of tracer microspheres subsequent to an intracoronary injection at a known flow rate. (RBCs can be radiolabeled by any known method.) First, the radiolabeled RBCs are injected and the radioactivity versus time distribution is measured and corrected to remove the influence of injection volume versus time distribution by deconvolution. Then, the tracer microspheres are injected and the videodensity versus time distribution is established. A deconvolution of the videodensity versus time distribution to remove the influences of the injection volume versus time distribution of the tracer microspheres and the corrected radiolabeled RBC volume versus time distribution, followed by normalization for differences in injection volume between radiolabeled RBCs and tracer microspheres, results in the ICTF. (See Example 3, infra.)

As indicated, it is advantageous to use 3-D echocardiography with the externally calibrated method. This advantage stems from the fact that the reference technique, radiolabelled blood cells, determines blood flow from a volume that may not strictly correspond to the volume represented by the area within a tomographic ultrasound image. If the scintillations are detected using a computed tomography technique, then the observed radiolabelled red blood cell volume vs. time distribution can be determined for the same volume interrogated ultrasonically using conventional 2-D imaging equipment and the ICTF can be established. If, however, the scintillations are detected using a planar technique, then the volume from which the scintillations are detected is not completely contained within the tomographic image, potentially resulting in an inaccurate estimate of the ICTF; the planar scintillation volume, however, can be used as the region of interest within a 3-D ultrasound image, for accurate determination of the ICTF.

The next step in the external calibration of tracer microspheres is to determine the IVTF. This function defines the changes in the relationship between videodensity and tracer microsphere volume which occur when the tracer microspheres flow from the site of injection to the myocardium. These changes might be due to exposure to the blood, passage through the lungs, dilution of the bolus and/or other physiological effects which occur during transit.

To establish the IVTF, the videodensity versus time distribution in the myocardium is first established following an intravenous injection of tracer microspheres. Then, a deconvolution is performed on the videodensity versus time distribution to remove the influences of the injection volume versus time distribution, the corrected radiolabeled RBC volume versus time distribution and the ICTF. (See Example 4, infra.)

Once the ICTF and IVTF have been established, i.e. the tracer microspheres have been calibrated, the myocardial blood flow in a test subject can be determined. (See Example 5, infra.) First, the videodensity versus time distribution in the myocardium is established following an intravenous injection of calibrated tracer microspheres.

Once the videodensity versus time distribution is established, a deconvolution is performed to remove the influence of the injection volume versus time distribution, the ICTF and the IVTF. This establishes the relationship between tracer microsphere volume versus time resulting solely from myocardial blood flow. Knowing this, the absolute myocardial blood flow rate can be calculated.

The following examples further illustrate the invention method. These examples are not intended to limit the invention in any manner.

EXAMPLE 1

Method of Making Microspheres By Mechanical Cavitation

Tracer microspheres containing various gases were produced as follows: 5% human albumin solution (USP) was deaerated under continuous vacuum for two hours. The vacuum was released by filling the evacuated vessel with the gas of interest. The albumin solution was adjusted to 68° C. via an inline heat exchanger and pumped at 100 mL/min into a 2" colloid mill (Greerco, Hudson N.H., model W250V or AF Gaulin, Everett, Mass., model 2F). The specific gas, at room temperature, was added to the liquid feed just upstream of the inlet port at a flow rate of 120–220 mL/min. The gap between the rotor and the stator was adjusted to 2/1000th inch and the albumin solution was milled continuously at about 7000 rpm at a process temperature of 73° C.

The dense white solution of microspheres thus formed was immediately chilled to a temperature of 10° C. by a heat exchanger, and collected in glass vials. The vials were immediately sealed. The material was characterized with regard to concentration and size distribution using a Coulter Counter (Coulter Electronics Inc., Haileah, Fla.). The results are shown in Table 3.

TABLE 3

|  | CONCENTRATION | MEAN SIZE, MICRONS |
| --- | --- | --- |
| Perfluoropropane | $8.3 \times 10^8$ | 3.8 |
| Perfluoroethane | $10.6 \times 10^8$ | 4.0 |
| Sulfur Hexafluoride | $8.4 \times 10^8$ | 3.9 |

EXAMPLE 2

Pressure Stability of Tracer Microspheres

Microspheres containing various gases were prepared as described in Example 1. Each sample of microspheres was diluted to an equal volume of encapsulated gas per mL of 0.15M phosphate-buffered saline (about 1:60 dilution) and an initial optical density measurement at 600 nm ($OD_{600}$) was recorded (Time 1). The diluted suspension was then subjected to a pressure of 5.0 psig (250 mm Hg) in a sealed vessel with adequate head space for thirty (30) seconds. A second $OD_{600}$ measurement was recorded immediately before release of the pressure (Time 2). After release of pressure and stabilization of the $OD_{600}$, a third measurement was taken (Time 3). Table 4 below shows the effect of 5.0 psig pressure on microsphere concentration as measured by the change in $OD_{600}$. The values reported in Table 4 represent the observed $OD_{600}$ at Time 2 or Time 3 divided by the initial $OD_{600}$ at Time 1 and are expressed as a percentage (%OD). This is a measure of the percent survivorship of the tracer microspheres at 5.0 psig.

TABLE 4

| GAS | % OD$_{600}$ at Time 2 | % OD$_{600}$ at Time 3 |
| --- | --- | --- |
| AIR | 0 | 0 |
| ARGON | 0 | 0 |
| SULFUR HEXAFLUORIDE | 8 | 30 |
| PERFLUOROETHANE | 63 | 78 |
| PERFLUOROPROPANE | 58 | 82 |
| PERFLUOROBUTANE | 60 | 87 |

These results demonstrate that microspheres containing the insoluble gases sulfur hexafluoride, perfluoroethane, perfluoropropane, and perfluorobutane are much more pressure-resistant than air or argon-filled microspheres.

The results for % OD$_{600}$ at Time 3 which reflect a higher % OD$_{600}$ than at Time 2, suggest that upon release of the pressure, the microspheres resume their original shape and volume. This has been confirmed by microscopic examinations of microsphere suspensions during and after application of pressure.

EXAMPLE 3

Determination of the Intracoronary Transfer Function (ICTF)

Step 1: Determination of the Relationship between Radiolabeled Red Blood Cell Volume Versus Time in the Myocardium A dog weighing approximately 25 kg was anesthetized with 30 mg/kg of sodium pentobarbital. A left thoracotomy was performed and the heart was suspended in a pericardial cradle. The proximal left coronary circumflex artery (LCX) was dissected free from the surface of the myocardium and two silk ties were placed around the vessel. The right carotid artery was exposed and a cannula was inserted into the arterial lumen and secured with silk ties. The proximal end of the carotid cannula was further connected to plastic tubing. A cannula which has two common input ports that merge into a single output port was attached to the distal end of the plastic carotid tubing. A segment of the tubing was placed in a roller pump to allow a controlled, predetermined flow rate. The tubing was primed with blood from the carotid artery and the LCX was ligated. The single output port of the cannula was inserted into the LCX distal to the site of ligation and secured with silk ties. Flow to the LCX was then adjusted via the roller pump to approximate a normal basal flow rate. An electromagnetic flow probe (model EP406, Carolina Medical King, N.C.) was placed distally around the isolated segment of the LCX to measure actual blood flow, which was determined to be 50 ml per second. The tubing supplying blood to the LCX was further connected to side-tubing which was connected to a power injector (model 3000, Liebel-Flarsheim, Cinncinnati, Ohio).

Prior to the animal preparation described above, fifty (50) ml of blood were collected from the dog and centrifuged to separate the red blood cells ("RBCs"). The RBCs were then labeled ex-vivo with technetium-99m. The labeled RBCs were then washed several times to reduce the unbound technetium-99m to less than 0.5% of the entire activity. One ml of labeled RBCs contained approximately 100 µCi of radioactivity.

A miniature gamma probe consisting of a CsI$_2$ scintillation crystal optically coupled to a photodiode and a 1 cm long converging collimator (Oakfield Instruments, Oxford, England) was used to measure RBC flow. The gamma probe head was placed within 3 cm of the anterior surface of the heart. One mL of radiolabeled RBCs was introduced into the LCX via the side-tubing at a rate of 2 mL per second, and radioactivity flow data was collected within the linear response range (below approximately 40,000 counts per second.)

Step 2: Determination of the Relationship between Videodensity Versus Time subsequent to an Intracoronary Injection Using the same dog from Example 3 Step 1, a saline bath was placed over the exposed heart to act as an acoustic interface between the ultrasound transducer and the anterior surface of the heart. A General Electric RT5000 (Waukesha, Wis.) Ultrasonograph was employed in the B-mode with a 5 MHz sector-array transducer probe. The depth was set to 4 cm to allow visualization of only the anterior portion of the myocardium. Image acquisition was initiated and images were recorded at a frame rate of 30 frames per second throughout the procedure and stored on S-VHS tape for later processing.

Tracer microspheres containing perfluoropropane were prepared according to U.S. Pat. No. 4,957,656 and diluted 1:50 with sterile saline. A 0.3 ml volume of diluted tracer microspheres was loaded into the side-tubing and injected at a flow rate of 2 ml per second. Image acquisition was discontinued after the videodensity of the myocardium returned to the pre-injection (baseline) level.

Step 3: Calculation of the intracoronary Transfer Function

The flow rate during the injection of radiolabeled RBCs in Step 1 was 52 ml/sec (the coronary artery flow rate (50 ml/sec) plus the injection flow rate (2 ml/sec)). With an injection time of 0.5 sec for the 1 ml of radiolabeled RBCs containing 100 µCi, the final concentration of radioactivity in the coronary artery was equal to 3.85 µCi/ml (100 µCi divided by 52 ml/sec times 0.5 sec). This factor allowed the conversion of the collected transit rate data into a radiolabeled RBC volume versus time distribution and is shown in FIG. 1. The data was fit to a gamma variate curve which resulted in the following; A=434 ml/sec$^2$, $t_o$=1.29 sec and α=0.407 sec$^{-1}$. The curve is also depicted in FIG. 1. From this fit, data points at 0.1 second intervals were derived.

Figure 2:
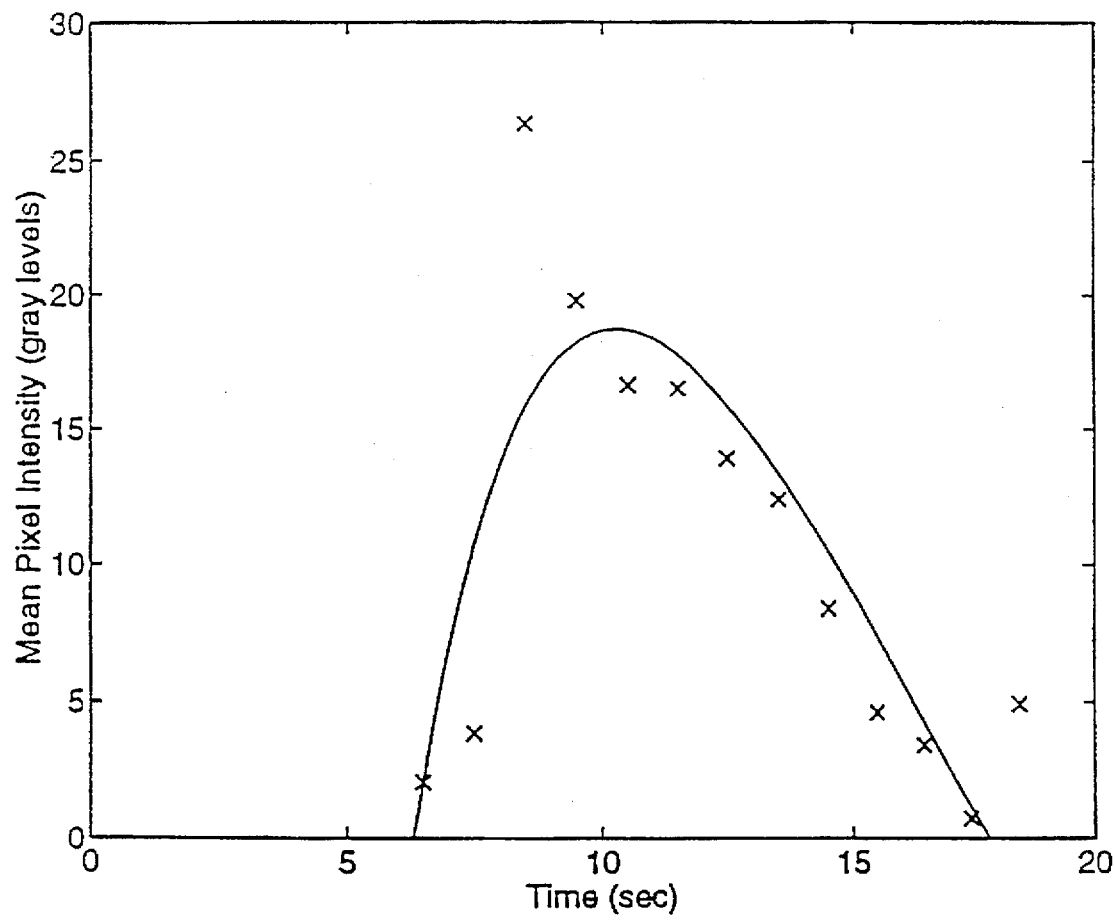

The images acquired in Step 2 of Example 3 were digitized (one frame per cardiac cycle), and the videodensity within the region of interest in the myocardial perfusion bed was averaged for each frame to give the mean pixel intensity (MPI). The videodensity versus time distribution after baseline videodensity subtraction is depicted in FIG. 2. The baseline subtracted data was fit to a gamma variate curve which resulted in the following; A=23.18 MPI/sec$^2$, $t_o$=0.94 sec and α=0.175 sec$^q$. The curve is also depicted in FIG. 2. From this fit, data points at 0.1 second intervals were again derived.

The radiolabeled RBC volume versus time distribution from Step 1 of Example 3 is set to $^{RBC}V_{obs}(t)$ and the radiolabeled RBC injection volume versus time distribution from Step 1 of Example 3 is set to $^{RBC}V_{inj}(t)$. In order to determine the distribution of radiolabeled RBCs which resulted solely from myocardial blood flow, i.e. the corrected radiolabeled RBC volume versus time distribution, $^{RBC}V_{flow}(t)$, the influence of injection volume versus time distribution was removed by a deconvolution as follows:

$$^{RBC}V_{flow}(t) = \mathfrak{F}^{-1}\left[\left[\frac{\mathfrak{F}[^{RBC}V_{obs}(t)]}{\mathfrak{F}[^{RBC}V_{inj}(t)]}\right]\right] \quad (1)$$

where F is the Fourier transform and F$^{-1}$ is the inverse transform.

Next, the videodensity versus time distribution from Step 2 of Example 3 is set to $^{TM}I_{obs}(t)$ and the tracer microsphere injection volume versus time distribution from Step 2 of Example 3 is set to $^{TM}V_{inj}(t)$, The injection volume of radiolabeled RBCs in Step 1 of Example 3, $V_{RBC}$, was equal to 1.0 ml, and the injection volume of tracer microspheres in Step 2, $V_{TM}$, was equal to 0.3 ml.

The ICTF, which is set to $T_{ic}(t)$, is then determined by a deconvolution of the injection volume versus time distribution and the videodensity versus time distribution from Step 2 of Example 3, and the corrected radiolabeled RBC volume versus time distribution from Step 1 of Example 3 as follows:

$$T_{IC}(t) = \Im^{-1}\left[\left[\frac{\Im[^{TM}I_{obs}(t)/V_{TM}]}{\Im[^{RBC}V_{flow}(t)/V_{RBC}]\Im[^{TM}V_{inj}(t)]}\right]\right] \quad (2)$$

Since the injection rates for both the radiolabeled RBCs and the tracer microspheres were the same (2 ml/sec), $^{RBC}V_{inj}(t)/V_{RBC}=^{TM}V_{inj}(t)/V_{TM}$. This allows Equation 2 to be simplified to:

$$T_{IC}(t) = \frac{D_{TM}V_{RBC}}{V_{TM}} \Im^{-1}\left[\left[\frac{\Im[^{TM}I_{obs}(t)]}{\Im[^{RBC}V_{obs}(t)]}\right]\right] \quad (3)$$

where $D_{TM}$ is the tracer microsphere dilution factor, which in the present example is equal to 50.

EXAMPLE 4

Determination of the Intravenous Transfer Function (IVTF)

Step 1: Determination of the Relationship Between Videodensity Versus Time Subsequent to an Intravenous Injection of Tracer Microspheres A dog weighing approximately 25 kg was anaesthetized with sodium pentobarbital and isoflurane, paralyzed with pancuronium bromide and artificially ventilated. Intravenous access from the internal jugular vein and a peripheral (cephalic) vein was maintained for the purpose of injecting tracer microspheres and administering fluids.

The heart rate from electrocardiographic monitoring and arterial blood pressure were recorded before and after injection of the tracer microspheres. Arterial blood gas analysis was performed every 15 minutes with adjustments made in ventilator settings as needed to maintain normal acid-base status and adequate oxygenation. The heart rate and blood pressure did not fluctuate from expected physiological values during the procedure.

Imaging was conducted with a Hewlett Packard Sonos 1500 (Andover, Mass.) Ultrasonograph in the B-mode using a transthoracic 5.0 MHz transducer. Image acquisition was initiated and images were recorded at a frame rate of 30 frames per second throughout the procedure and stored on S-VHS tape for later processing.

Tracer microspheres containing perfluoropropane were prepared according to U.S. Pat. No. 4,957,656. A 1.0 ml volume of tracer microspheres was injected into the cephalic vein at a rate of 0.3 ml per second. Image acquisition was discontinued after the videodensity of the myocardium returned to the pre-injection (baseline) level.

Step 2: Calculation of the Intravenous Transfer Function

Figure 3:
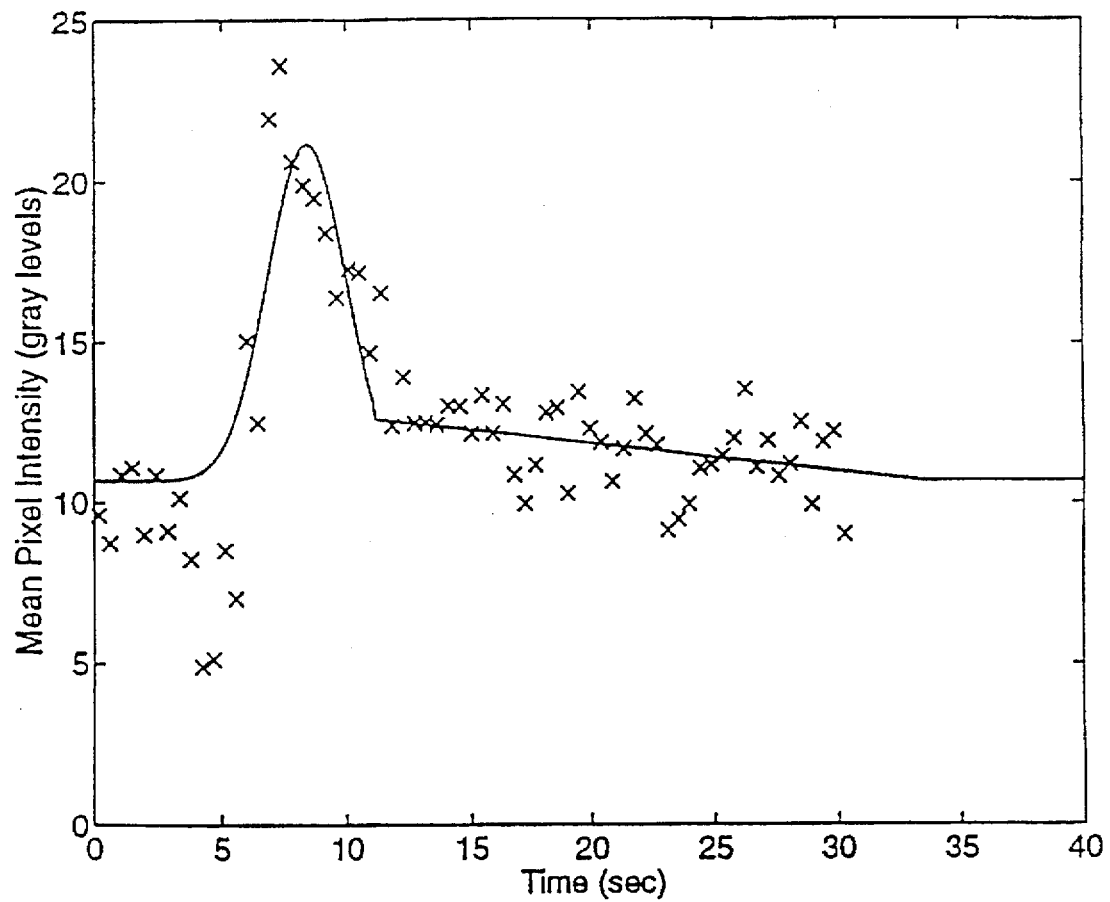

The images acquired in Step 1 of Example 4 were digitized (one frame per cardiac cycle), and the videodensity within the region of interest in the myocardial perfusion bed was averaged for each frame to give the mean pixel intensity (MPI). The videodensity versus time distribution is depicted in FIG. 3. The data was fit to a curve of the form:

$$^{TM}I_{obs}(t) = A_3 + \frac{A_0}{\sqrt{A_2}} e^{[-(\frac{t-A_1}{A_2})^2]} \quad (4)$$

for $0<t<21.5$ sec, with $A_0=15.60$ MPI·sec$^{1/2}$, $A_1=18.83$ sec, $A_2=2.21$ sec, and $A_3=10.68$ MPI.

For $t \geq 21.5$ sec, the data was fit to a line:

$$^{TM}I_{obs}(t) = A_4 + A_5 t \quad (5)$$

with $A_4=14.41$ MPI and $A_5=-0.86$ MPI/sec. The curve is also depicted in FIG. 3.

The videodensity versus time distribution after subtraction of baseline videodensity is set to $^{TM-IV}I_{obs}(t)$, and the injection volume versus time distribution is set to $^{TM-IV}I_{inj}(t)$. The total injected volume of tracer microspheres, $V_{TM-IV}$, is equal to 1.0 ml.

The IVTF, which is set to $T_{IV}(t)$, is determined by a deconvolution of the videodensity versus time distribution and the injection volume versus time distribution from Example 4 Step 1, the corrected radiolabeled RBC volume versus time distribution from Example 3 Step 1, and the ICTF as follows:

$$T_{IV}(t) = \Im^{-1}\left[\left[\frac{\Im[^{TM-IV}I_{obs}(t)/V_{TM-IV}]}{\Im[^{RBC}V_{flow}(t)]\Im[^{TM-IV}V_{inj}(t)]\Im[T_{IC}(t)]}\right]\right] \quad (6)$$

EXAMPLE 5

Determination of Myocardial Blood Flow in a Test Subject

Step 1: Determination of the Relationship between Videodensity versus Time subsequent to an IV Injection of Tracer Microspheres Images were acquired in a test subject as described in Step 1 of Example 4 with the following variation:

The heart was exposed through a left thoracotomy and the pericardia were opened and secured. The left anterior descending coronary artery was exposed and a total occlusion was produced with a ligature in order to mimic the effects of a coronary artery disease-induced reduction in myocardial blood flow. The occlusion was released after five minutes, and the tracer microspheres were immediately injected into the cephalic vein.

Step 2: Calculation of Myocardial Blood Flow

Figure 4:
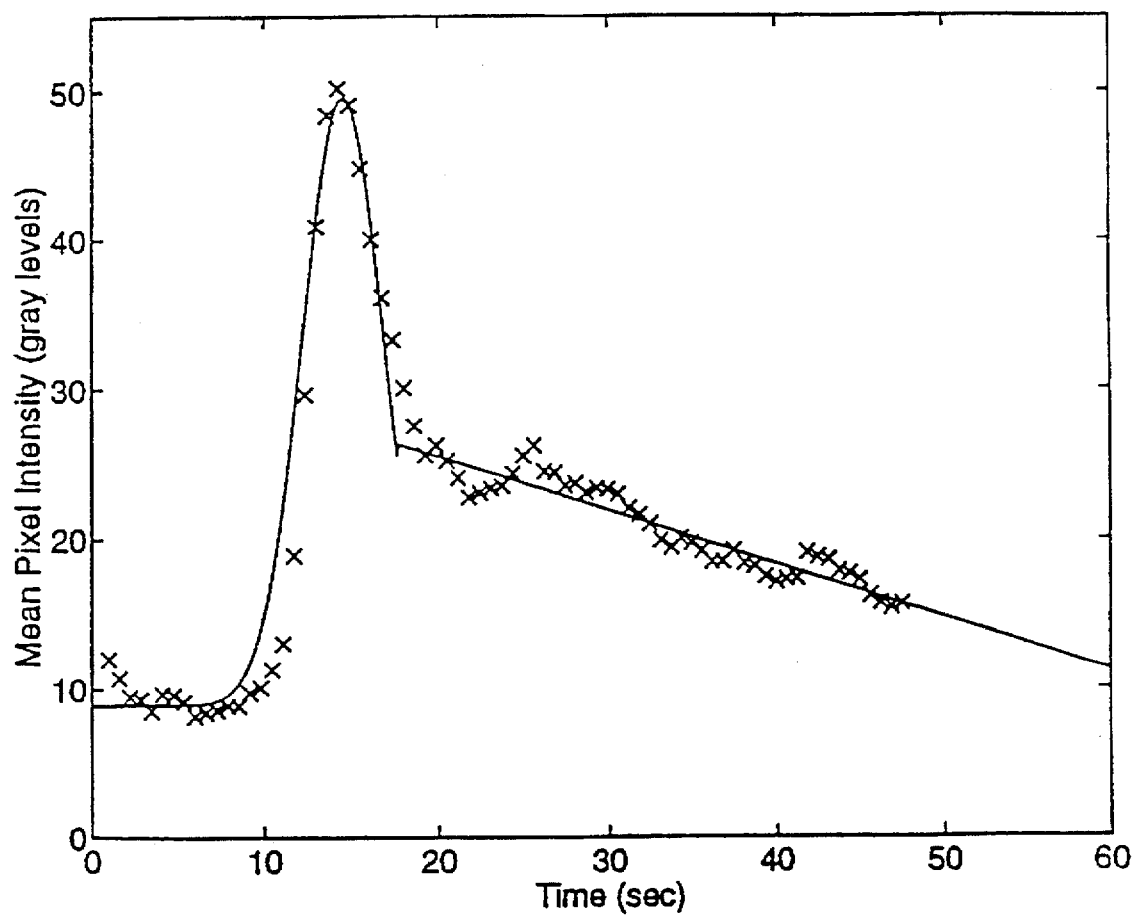

The images acquired in Example 5 Step 1 were digitized (one frame per cardiac cycle), and the videodensity within the region of interest in the myocardial perfusion bed was averaged for each frame to give the mean pixel intensity (MPI). The resultant videodensity versus time distribution is depicted in FIG. 4. The data was fit as described in Example 3 Step 2 to a curve for $0<t<19$ seconds, and to a line for $t \geq 19$ seconds. This resulted in; $A_o=73.49$ MPI·sec$^{1/2}$, $A_1=14.72$ sec, $A_2=3.27$ sec, $A_3=8.89$ MPI, $A_4=32.61$ MPI and $A_5=-0.36$ MPI/sec. The resultant curve is also depicted in FIG. 4.

The videodensity versus time distribution in the test subject after subtraction of baseline videodensity is set to $^{TEST}I_{obs}(t)$, and the injection volume versus time distribution is set to $^{TRST}I_{inj}(t)$. The total injected volume of tracer microspheres, $V_{TES}$, is equal to 1.0 ml.

The tracer microsphere volume versus time distribution, $^{TEST}V_{flow}(t)$, which results solely from myocardial blood flow, is given by a deconvolution of the videodensity versus time distribution, the injection volume versus time distribution, the ICTF and the IVTF, as follows:

$$\text{TEST}V_{flow}(t) = \Im^{-1}\left[\left[\frac{\Im[\text{TEST}I_{obs}(t)/V_{TEST}]}{\Im[T_{IV}(t)]\Im[\text{TEST}V_{inj}(t)]\Im[T_{IC}(t)]}\right]\right] \quad (7)$$

Figure 5:
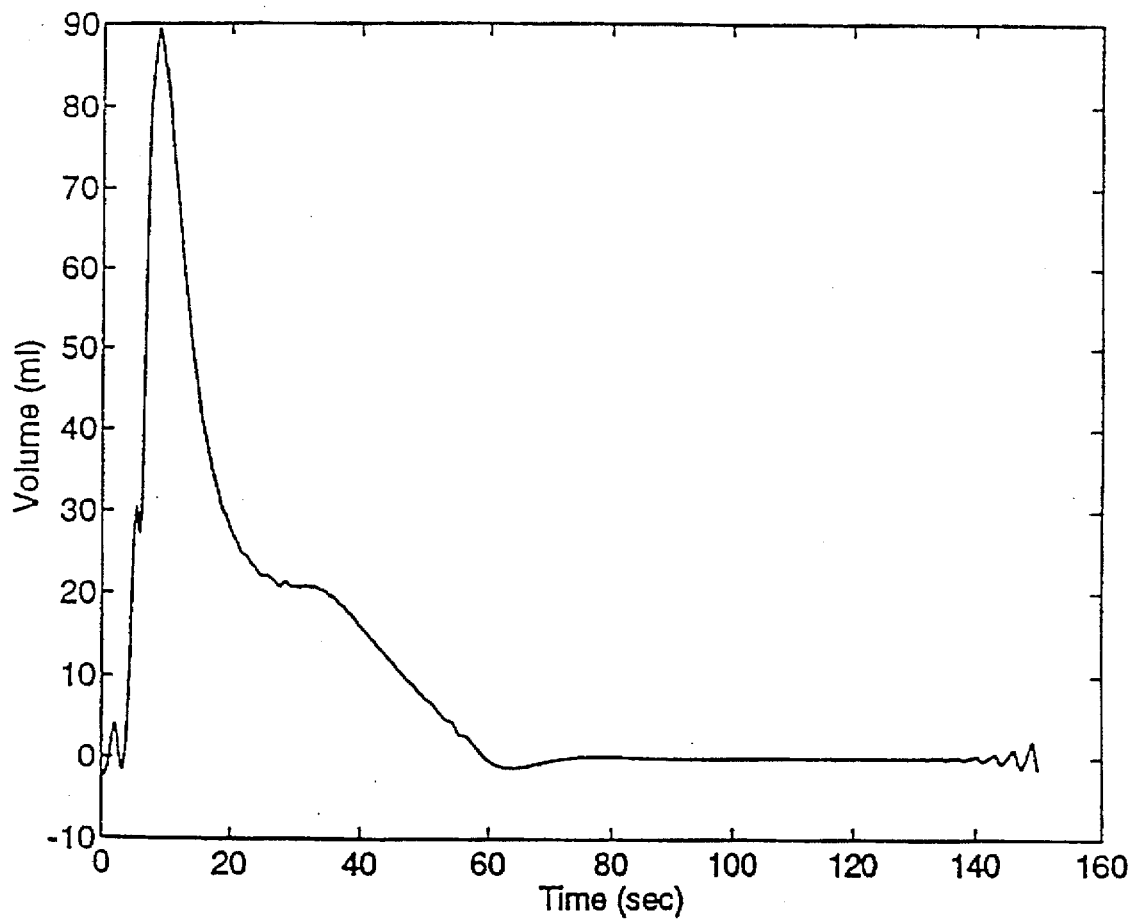

The resultant distribution is depicted in FIG. 5. Once $\text{TEST}V_{FLOW}(t)$ has been determined, the myocardial blood flow rate, BFR, can be determined as follows:

$$BFR = \frac{\left[\int_0^\infty \text{TEST}V_{FLOW}(t)dt\right]^2}{\int_0^\infty t \cdot \text{TEST}V_{FLOW}(t)dt} \quad (8)$$

In the present example, the calculated BFR is equal to 68 ml per sec, which is in accord with the expected flow rate following a hyperemic episode.

We claim:

1. A method of quantitatively measuring blood flow in the myocardium of a patient comprising:
   (a) initiating ultrasonic imaging of the myocardium;
   (b) while said imaging is continued, intravenously injecting an effective dosage of a suspension of biocompatible tracer microspheres containing an insoluble gas into the patient, wherein:
      (i) the microspheres have a mean diameter that permits them to pass through the pulmonary capillaries of the patient and
      (ii) said suspension is capable of maintaining 25% of the initial optical density at 600 nm after being subjected to a pressure of 5 psi for 30 seconds;
   (c) continuing said imaging during the first transit of the microspheres through the myocardium;
   (d) determining a videodensity versus time relationship from the images obtained in steps (a) through (c); and
   (e) calculating the blood flow in the myocardium from said relationship.

2. The method of claim 1 wherein the microspheres have a mean diameter in the range of about 2 to about 10 micrometers.

3. The method of claim 1 wherein the microspheres have a mean diameter in the range of about 4 to about 7 micrometers.

4. The method of claim 3 wherein said suspension contains a microsphere concentration of $5\times10^7$ to $5\times10^9$ per mL and the dosage is in the range of 12 to 40 μL of said suspension per kg body weight of the patient.

5. The method of claim 1 wherein the microspheres are human serum albumin microspheres containing a perfluoroalkane gas.

6. The method of claim 5 wherein the gas is perfluoropropane.

7. The method of claim 5 wherein the microspheres have a mean diameter in the range of about to 7 micrometers, the microsphere concentration in the suspension is $5\times10^8$ to $1\times10^9$ per mL and the dosage is in the range of 20 to 32 μL of suspension per kg of body weight of the patient.

8. The method of claim 1 wherein the microspheres have a mean diameter in the range of about 2 to about 5 micrometers.

9. The method of claim 1 wherein the imaging is a three dimensional imaging procedure performed by any conventional three dimensional imaging device.

10. The method of claim 6 wherein the microspheres have a mean diameter in the range of about 2 to 5 micrometers, the microsphere concentration in the suspension is $5\times10^8$ to $1\times10^9$ per mL and the dosage is in the range of 20 to 32 μL of suspension per kg of body weight of the patient.

\* \* \* \* \*